(12) United States Patent
Davis et al.

(10) Patent No.: US 6,750,330 B1
(45) Date of Patent: Jun. 15, 2004

(54) LYOPHILIZED TUBULINS

(76) Inventors: Ashley Davis, Apt. 503, 2030 E. 11th Ave., Denver, CO (US) 80206; Kim Middleton, Apt. 503, 2030 E. 11th Ave., Denver, CO (US) 80206

( * ) Notice: Subject to any disclaimer, the term of this patent is extended or adjusted under 35 U.S.C. 154(b) by 0 days.

(21) Appl. No.: 09/310,981

(22) Filed: May 13, 1999

Related U.S. Application Data

(60) Provisional application No. 60/085,382, filed on May 14, 1998.

(51) Int. Cl.$^7$ .......................... C07K 14/47; C07K 1/32; C07K 1/36
(52) U.S. Cl. .................. 530/418; 530/350; 530/412
(58) Field of Search .................. 530/350, 412, 530/418; 435/4, 7.1

(56) References Cited

U.S. PATENT DOCUMENTS 5,908,826 A * 6/1999 Fukuda et al.

FOREIGN PATENT DOCUMENTS

EP  0417193  * 5/1998

OTHER PUBLICATIONS

Shelanski, et al. 1973, Proc Natl acad Sci, USA, 70(3):765–8.*
Boniifacino, et al., Current Protocols in Cell Biology, Johu wiley and Sons, Inc., Unit 13:1.*
Shelanski, et al., Mar. 1973, Proc. Natl. Acad. Sci., USA, vol 70:765–768.*
Davis, Ashley et al. "Purification and Biochemical Characterization of Tubulin from the Budding Yeast *Saccharomyces cerevisiae*", *Biochemistry* (1993), vol. 32, pp. 8823–8835.
Davis, Ashley et al. "Microtubule Dynamics Modulated by Guanosine Triphosphate Hydrolysis Activity of β–Tubulin" *Science* vol. 264, (May 6, 1994), pp. 839–842.
Dawson, Peter J. et al. "Purification and Characterisation of Tubulin from the Parasitic Nematode, *Ascaridia Galli*," *Molecular and Biochemical Parasitology*, vol. 7 (1983), pp. 267–277.
Lee, James C. et al. "In Vitro Reconstitution of Calf Brain Microtubules: Effects of Macromolecules" *Biochemistry*, vol. 17, No. 14, (Jul. 11, 1978), pp. 2783–2790.
Lubega, George W, et al. "Expression of cloned β–tubulin genes of *Haemonchus contortus* in *Escherichia coli*: interaction of recombinant β–tubulin with native tubulin and mebendazole", *Molecular and Biochemical Parasitology*, vol. 62 (1993), pp. 281–292.
Nogales, Eva, et al. "Structure of the αβ tubulin dimer by electron crystallography" *Nature*, vol. 391, (Jan. 8, 1998), pp. 199–203.
Schiff, Peter, et al. "Taxol stabilizes microtubules in mouse fibroblast cells" *Proc., Natl. Acad. Sci. USA*, vol. 77, No. 3, pp. 1561–1565 (Mar. 1980).
Shelanski, Michael et al. "Microtubule Assembly in the Absence of Added Nucleotides", Proc. Natl. Acad. Sci. USA, vol. 70, No. 3, (Mar. 1973); pp. 765–768.
Soifer, David, et al. "Enzymatic Activity in Tubulin Preparations", *Biochimica et Biophysica Acta*, vol. 271, (1972), pp. 182–192.
Tubulin, Sigma Chemical 1996 Catalog, Catalog No. T4925 1pg.
Wisenberg, Richard C., "Aggregation of Microtubule Subunit Protein. Effects of Divalent Cations, Colchicine and Vinblastine", *Biochemistry*, vol. 9, No. 21, (1970).
Weatherbee, James A., Purification and Reconstitution of HeLa Cell Microtubules, *Biochemistry*, vol. 19 (1980); pp. 4116–4123.

* cited by examiner

*Primary Examiner*—Mary E. Mosher
*Assistant Examiner*—Misook Yu

(57) ABSTRACT

Lyophilized active tubulin and numerous uses of lyophilized active tubulin such as diagnostic, therapeutic, drug discovery, and research applications are provided. The process of making the lyophilized active tubulin is also described.

34 Claims, 14 Drawing Sheets

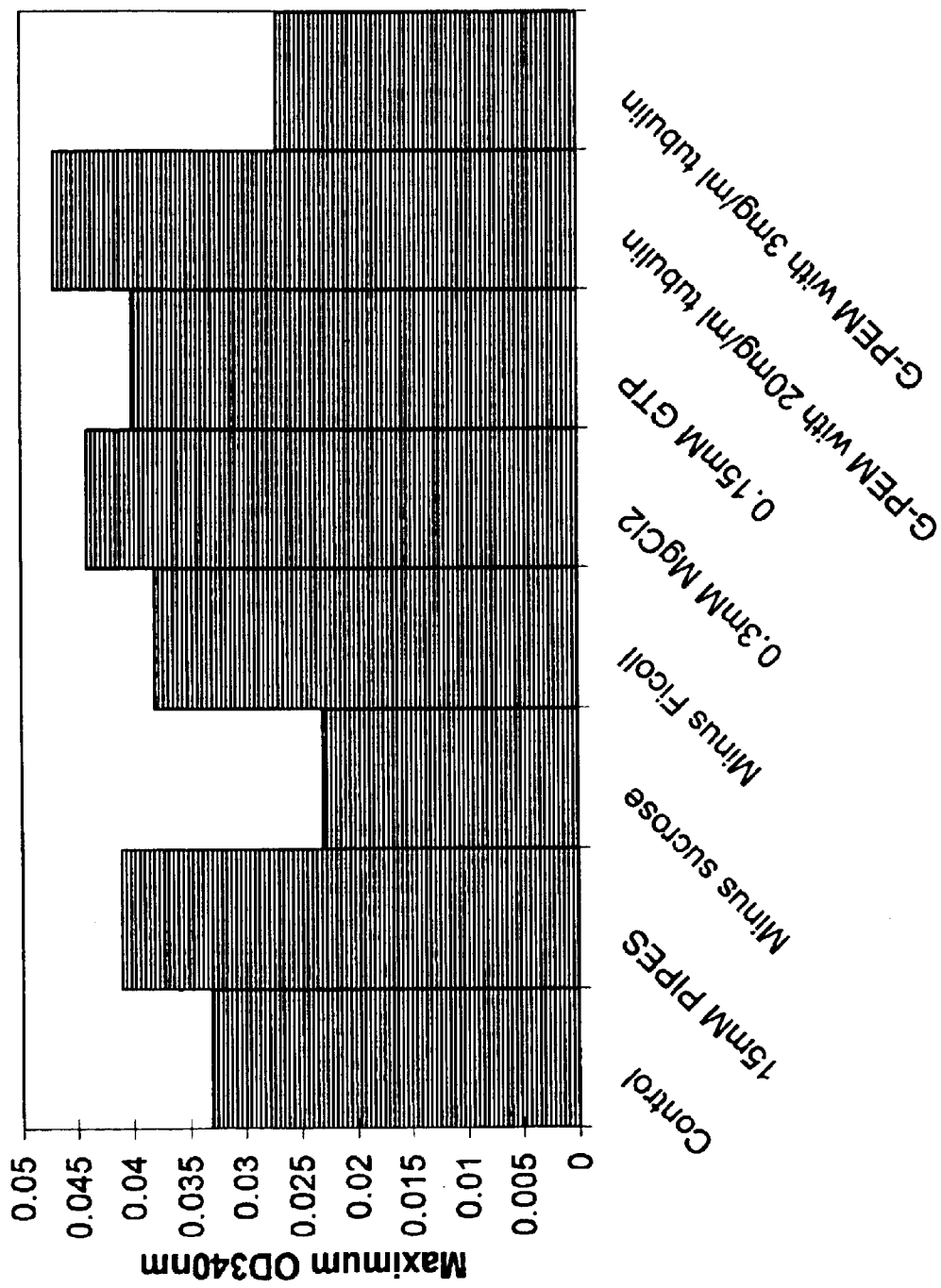

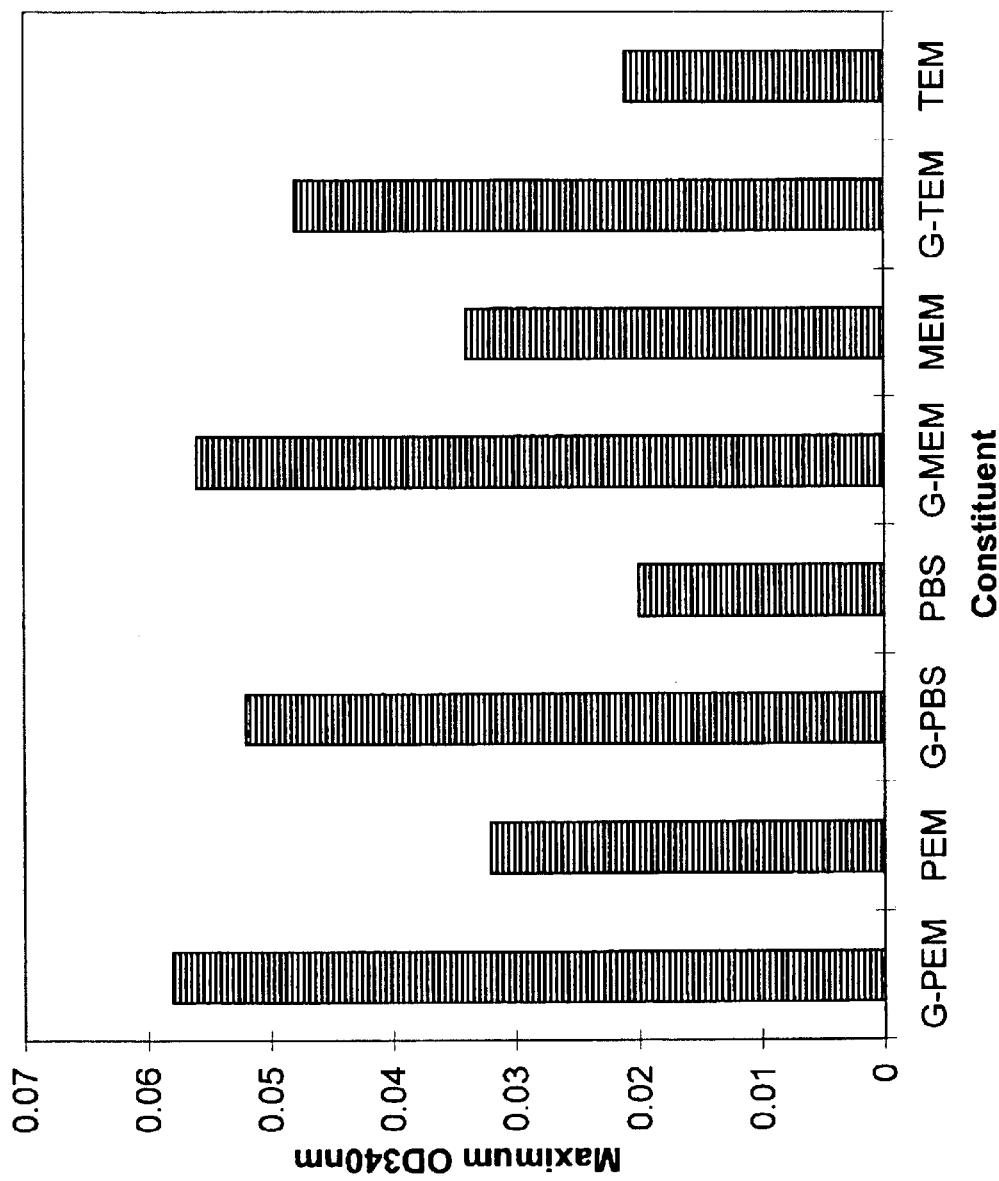

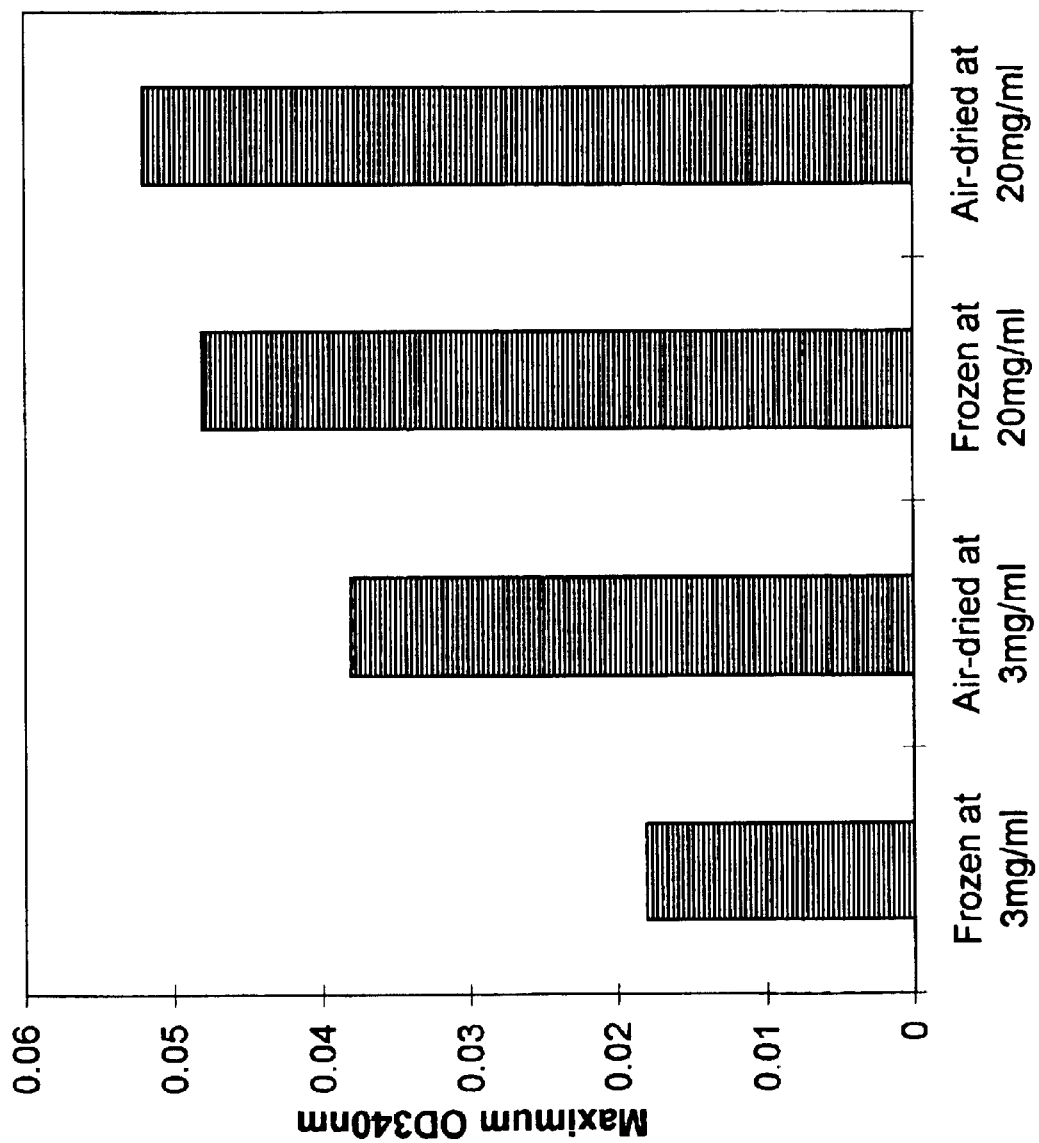

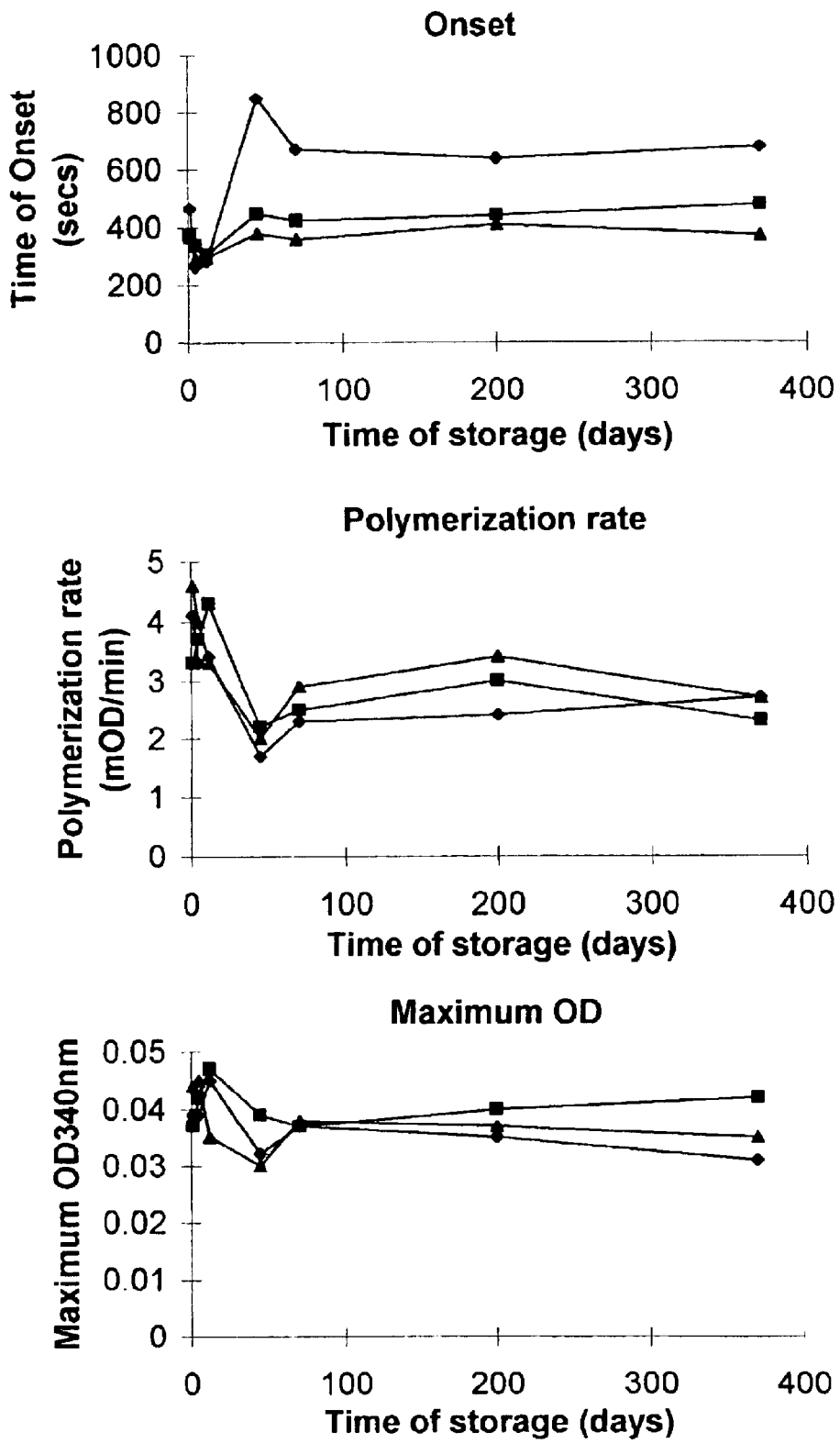
Figure 4 - Stability of different tubulin polymerization parameters during storage at different temperatures.

Figure 5 - Purity of different tubulin preparations.
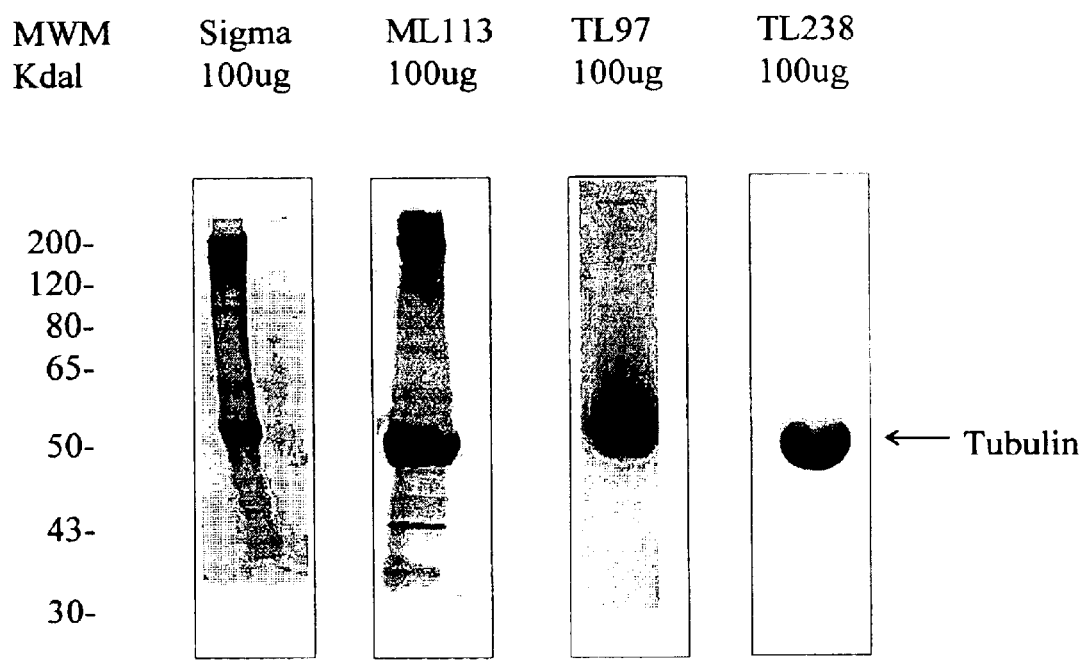

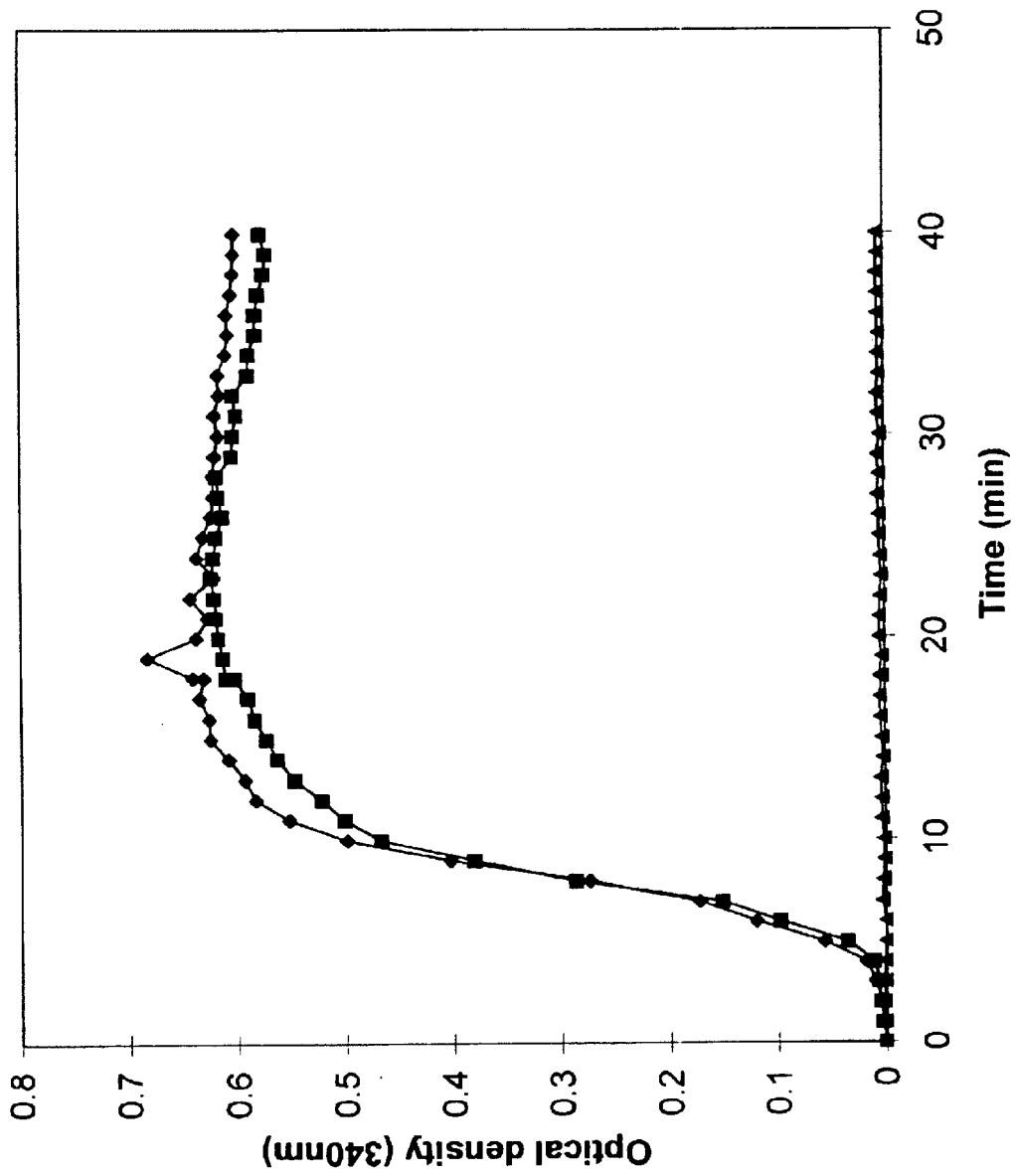

Figure 7 - Electron micrograph of polymerized tubulin samples
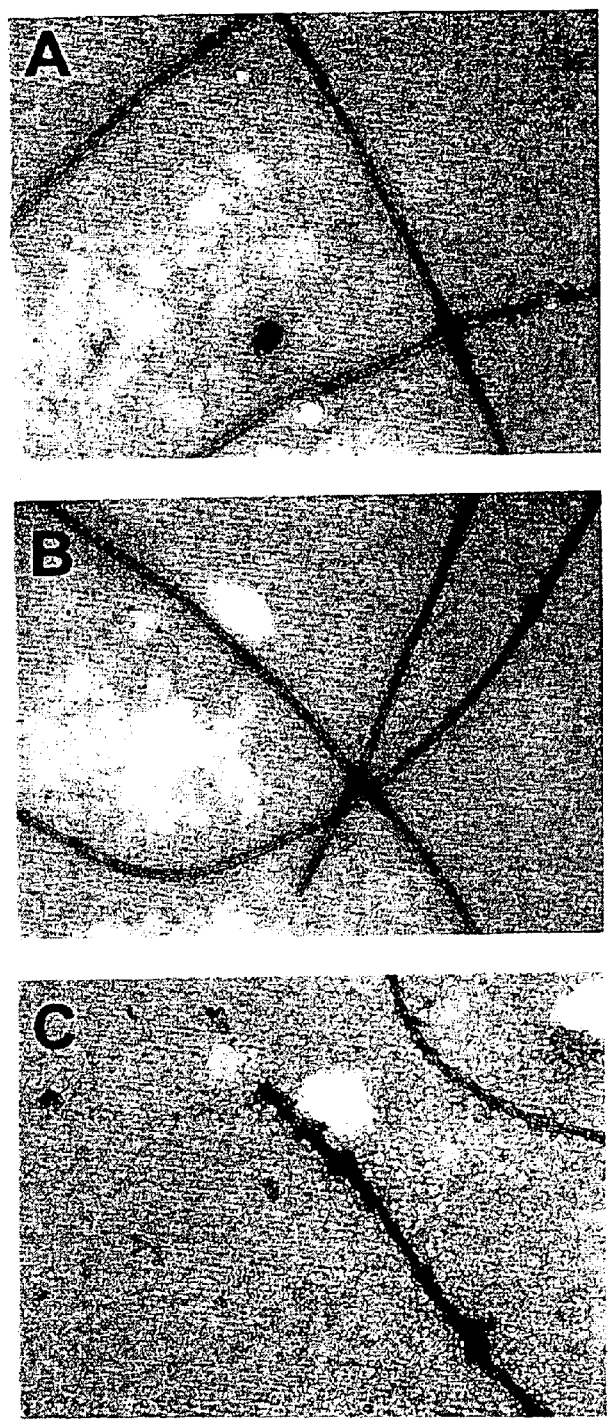

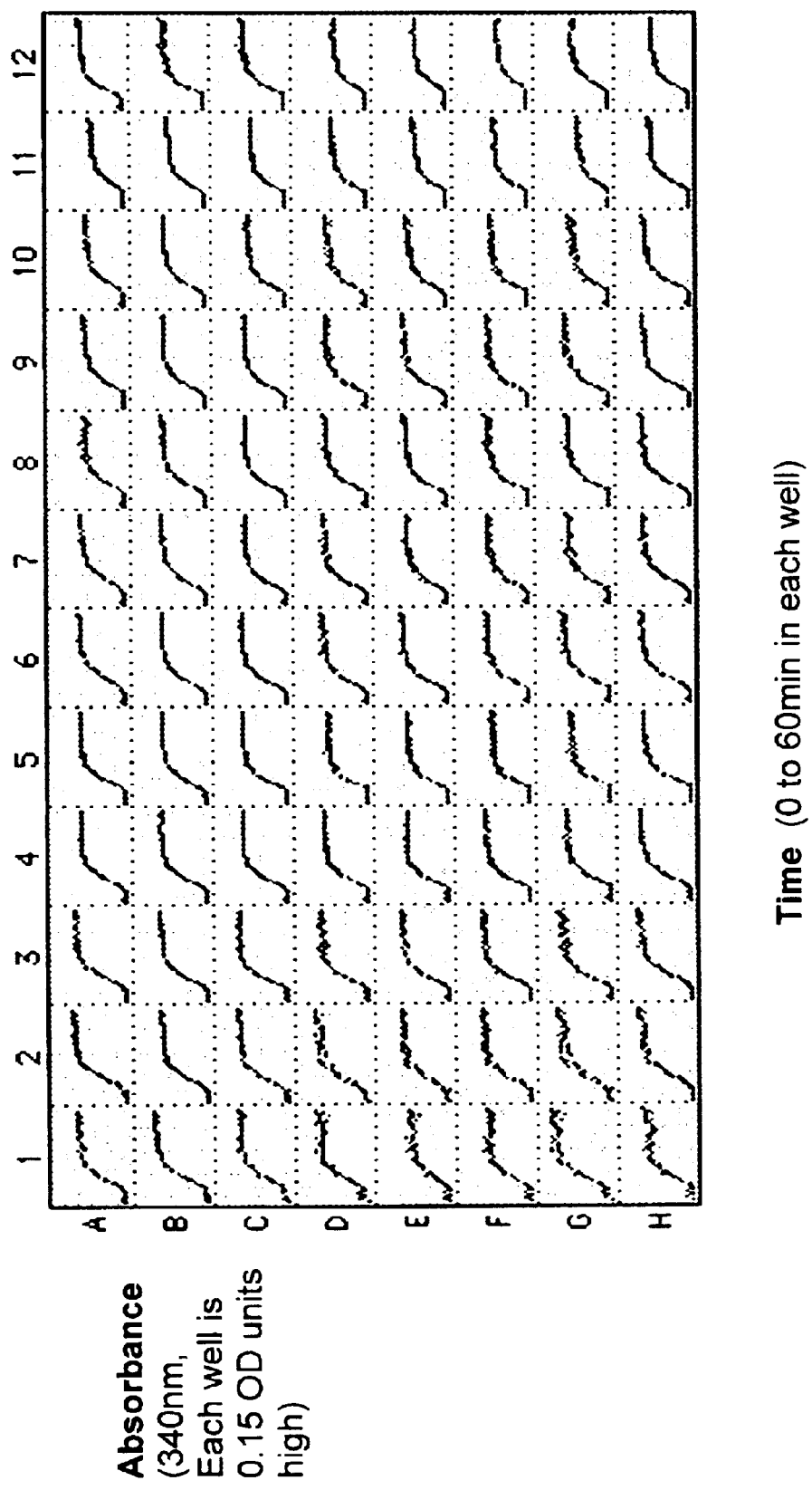
Figure 8 - Polymerization of tubulin by directly reconstituting tubulin that has been lyophilized in the wells of a 96-well plate.

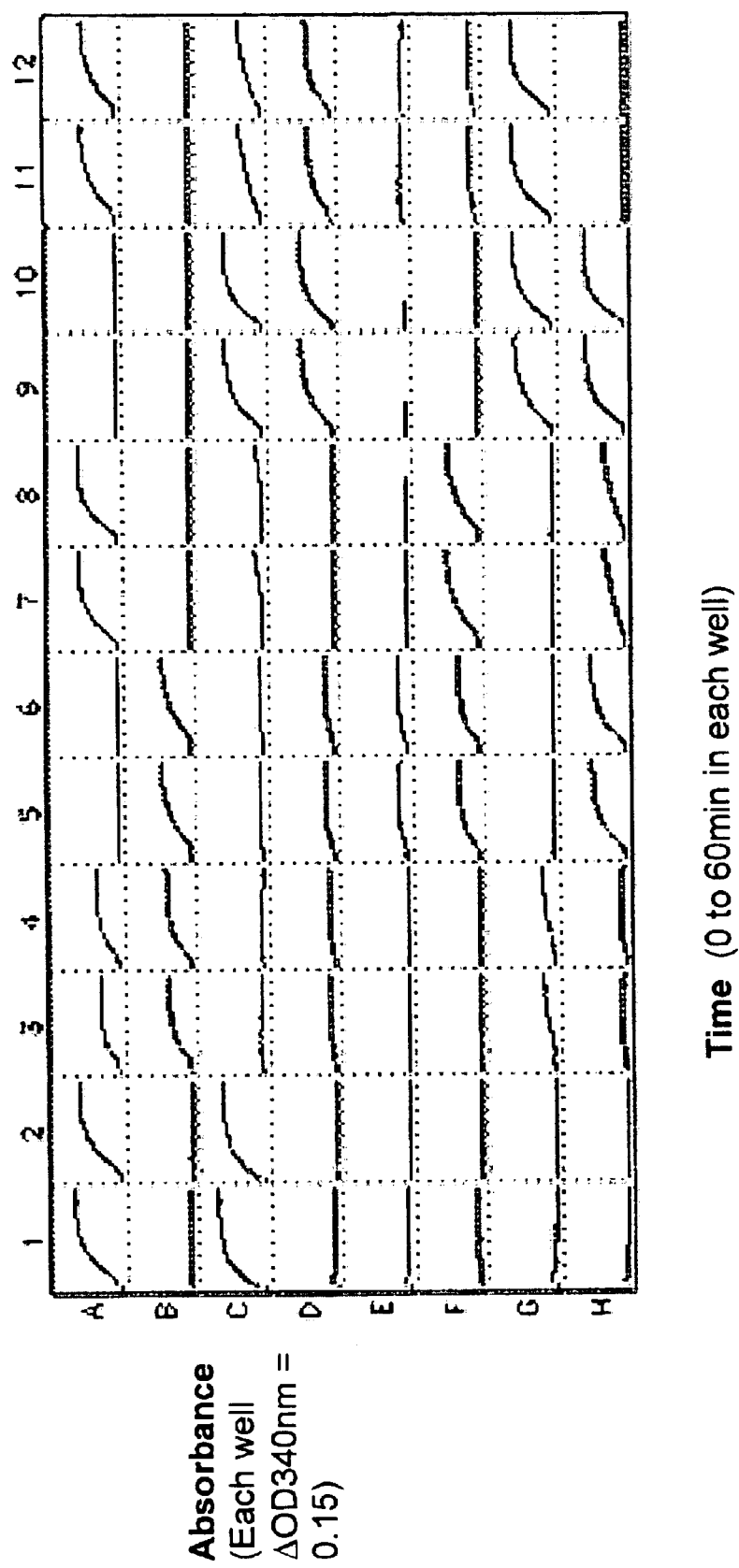
Figure 9 - Polymerization of tubulin by directly reconstituting tubulin that has been lyophilized in the wells of a 96-well plate: Duplicate reactions with buffer containing tubulin ligands.

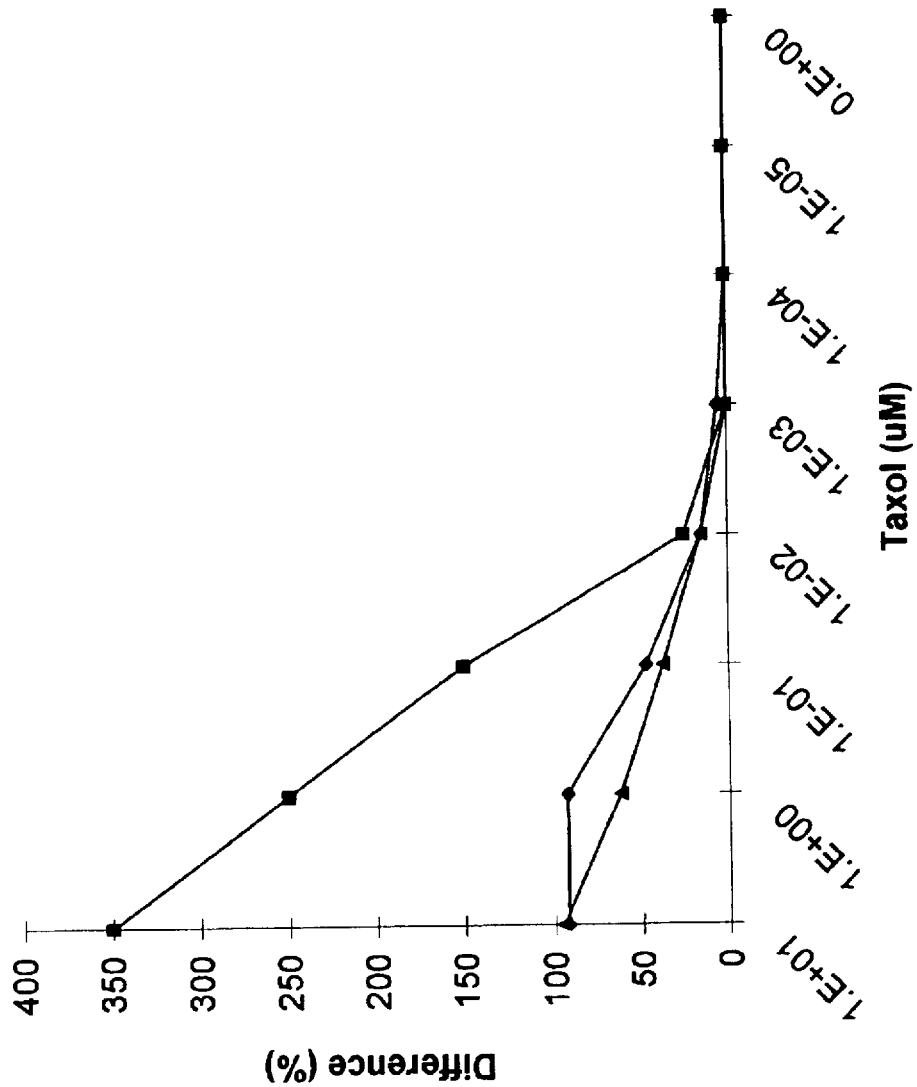

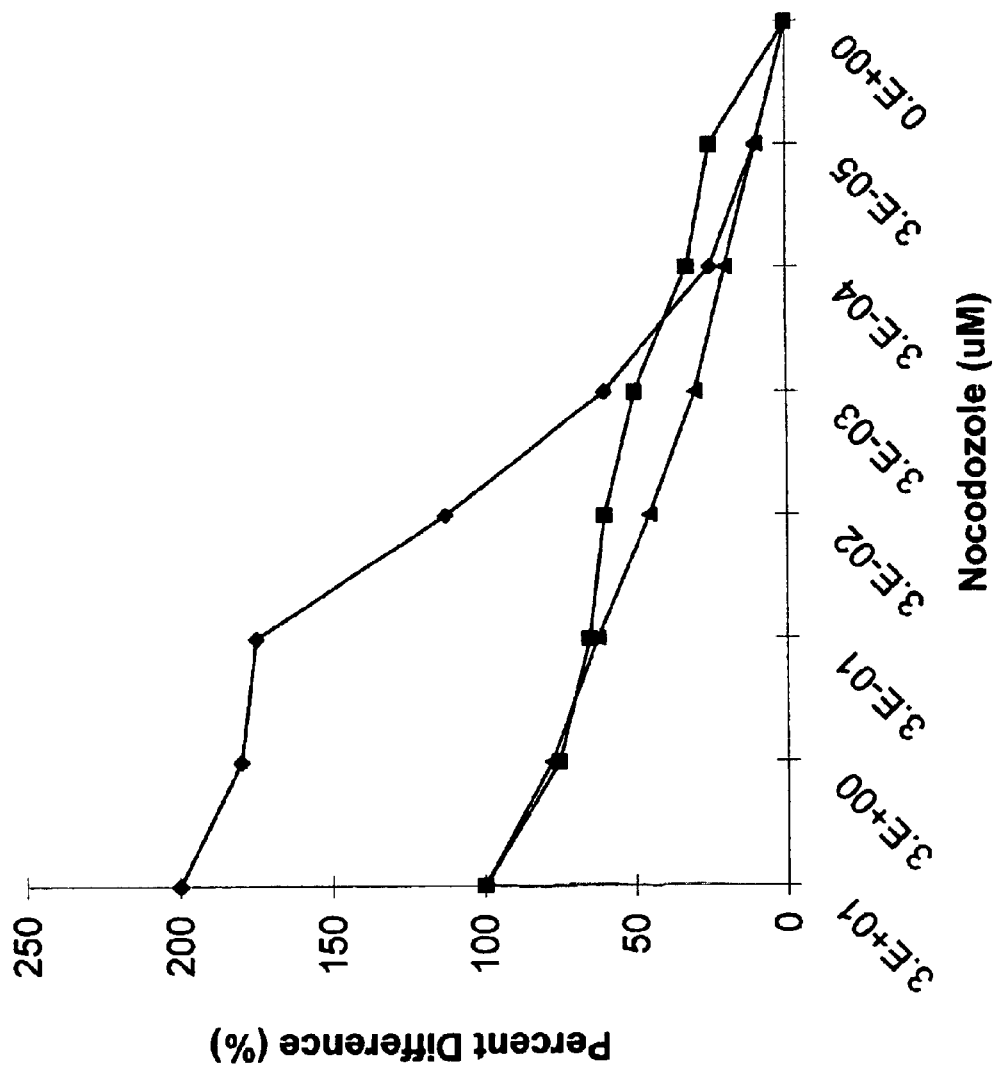

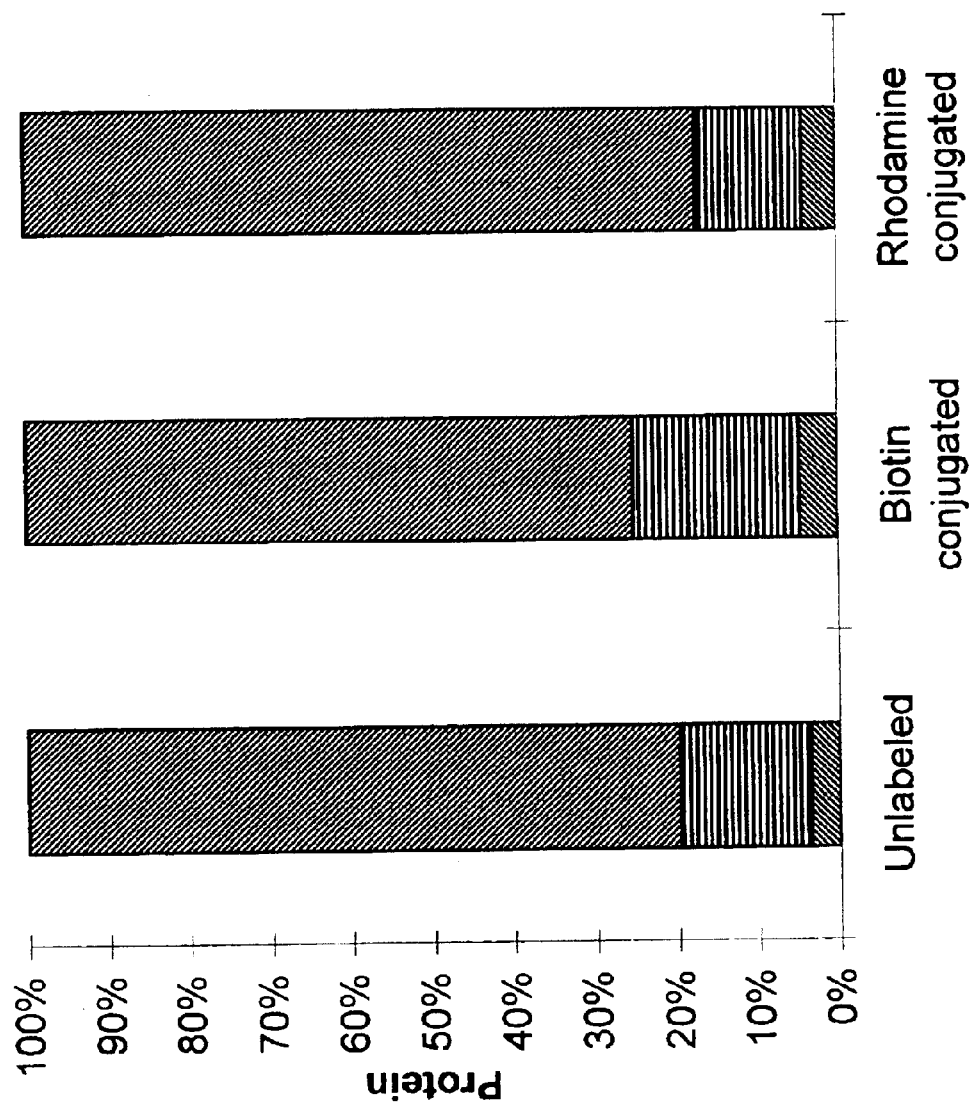

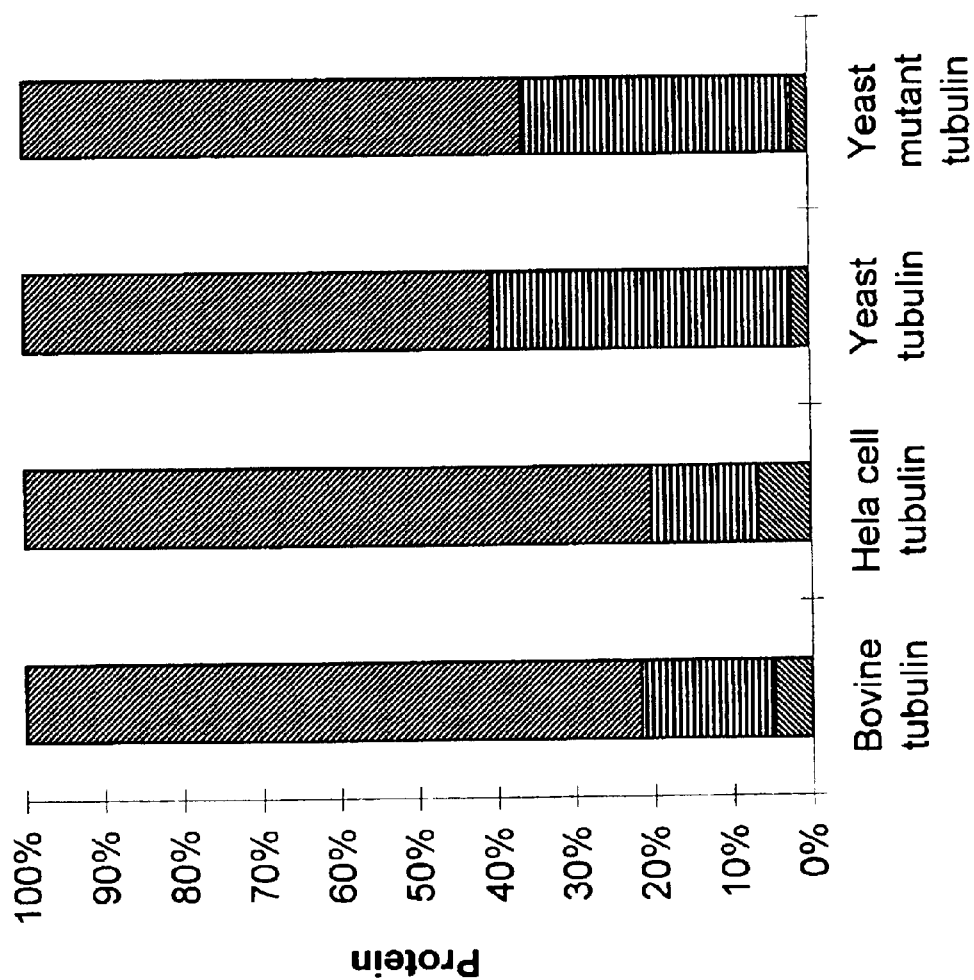
Figure 13 - Other sources of tubulin are ameniable to lyophilization

Figure 14 - Electron micrograph of lyophilized microtubules
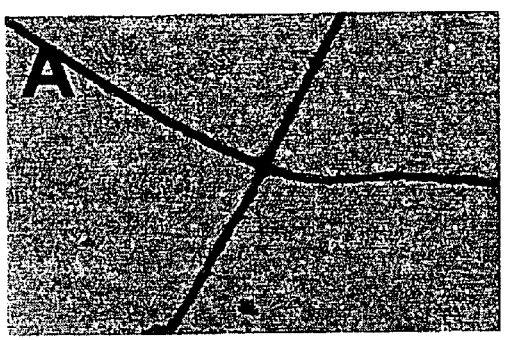
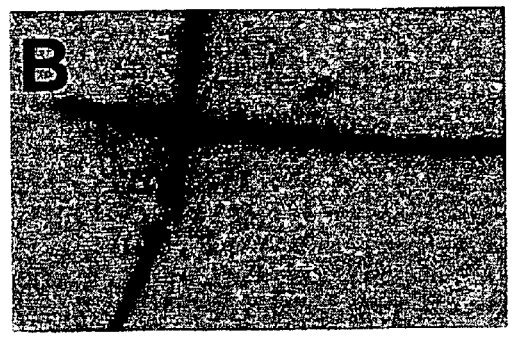

LYOPHILIZED TUBULINS

This application claims the benefits of the provisional application No. 60/085,382, filed May 14, 1998.

I. FIELD OF THE INVENTION

The present invention relates to the use of lyophilized active tubulin. More particularly, the present invention relates to the diagnostic and therapeutic applications of lyophilized active tubulin, and the use of lyophilized active tubulins in the fields of drug discovery and research.

II. DISCUSSION OF THE BACKGROUND ART

Tubulin is an essential intracellular protein that is necessary for mitosis, transport of intracellular material, cell structure, and cell motility. Tubulin is composed of a heterodimer of two closely related 55 Kilodalton proteins called alpha and beta tubulin. These two proteins are encoded by separate genes or small gene families, whose sequences are highly conserved throughout the eukaryotic kingdom.

Tubulin polymerizes to form structures called microtubules. When tubulin polymerizes it initially forms protofilaments. Microtubules consist of 13 protofilaments and are 25 nm in diameter, each $\mu$m of microtubule length being composed of 1650 tubulin heterodimers. Microtubules are highly ordered fibers that have an intrinsic polarity. There is a dynamic flux between microtubules and tubulin. When this equilibrium is perturbed by anti-tubulin agents like paclitaxel (taxol), cells will arrest in mitosis and eventually die. (Schiff et al., 1980, *Proceedings of the National Academy of Sciences USA*, 77, 1561–1565.) This is the mechanistic basis of how anti-tumor (TAXOL, vinblastine, and nocodazole), anti-fungal (benomyl) and anti-anthleminitic (mebendazole) agents interact with tubulin. Vinblastine, paclitaxel (TAXOL™ Bristol Myers-Squibb Co.), and nocodazole bind to tubulin and thus inhibit mitosis (Weisenberg, R. C., and S. N. Timasheff, 1970, *Biochemistry*, 21, 4110–4116; Schiff et al., 1980). These agents were identified through cell or organism based screens and were only later found to interact with tubulin.

Different forms of tubulin have been isolated. These include a microtubule associated protein (MAP)-rich tubulin that is 50% to 97% purified (Shelanski, M. L., Gaskin, F., and C. R. Cantor, 1973, *Proceedings of the National Academy of Sciences USA*, 70, 765–768), highly purified (97% to 99.99% or apparently 100% purified by silver stain or coomassie-blue stained SDS-PAGE) tubulin, e.g., Phosphocellulose purified tubulin (Lee, J. C., Tweedy, N., S. N. Timasheff, 1978, *Biochemistry*, 17(14), 2783–2790), tubulin from crude cancer cell line extracts (Weatherbee, J. A., Luftig, R. B., R. R. Weihing, 1980, *Biochemistry*, 19 (17), 4116–4123), tubulin isolated from higher eukaryotes and their cell lines (Weatherbee et al. 1980), tubulin isolated from fungi and yeasts and their cell lines (Davis, A., Sage, C. R., Dougherty, C., K. W. Farrell, 1993, *Biochemistry*, 32, 8823–8835), tubulin isolated from parasitic organisms or their cell lines (Dawson, P. J., Gutteridge, W. E., K. Gull, 1983, *Molecular and Biochemical Parasitology*, 7(3), 267–277), and tubulins isolated from recombinant systems and recombinant organisms (Davis, A., Sage, C. R., Dougherty, C., K. W. Farrell, 1994, *Science*, 264, 839–842.)

Although tubulin is the target of several anti-tumor, anti-fungal and anti-anthleminitic (anti-parasitic) agents, it has not been utilized as a target in high through-put drug screening programs, diagnostic screens, or therapy because of its lability. Tubulin is unstable and will denature, becoming inactive within two days at 4° C. (Shelanski et al., 1973.) Attempts have been made to create lyophilized forms of tubulin that are stable at room temperature. Since the first purification of tubulin by Weisenberg and Timasheff in 1970, several attempts at tubulin lyophilization have been recorded. The first by Weisenberg and Timasheff in 1970 involved crude lyophilizations on impure tubulin preparations at 97% purity (Weisenberg et al., 1970). This study did not result in assembly of competent tubulin. The second attempt in 1972 by Soifer et al. involved the reconstitution of tubulin into physiological buffer but resulted in no microtubule formation (Soifer, D., Laszlo A. H., J. M. Scotto, 1972, *Biochimica et Biophysica Acta*, 271, 182–192). Thus, the resulting protein was, incompetent for assembly and, therefore, inactive. Following Weisenberg et al. and Soifer et al., the dogma in tubulin biochemistry has been that highly purified tubulin cannot be lyophilized with high activity. In 1996, Sigma Chemical Company, St. Louis, Mo. (Sigma) introduced a 30–40% crude preparation of tubulin (Tubulin, *Sigma Chemical Company* 1996 *Catalog*, Catalog No. T4925). The product profile for T4925 (Lot. No. 87H4024) states that microtubules are formed upon reconstitution. However, comparative laboratory studies between T4925 and the lyophilized tubulin of the present invention disclosed herein have shown that the tubulin has very low activity as tested by a polymerization assay and very few microtubules are visible by electron microscopy. Thus, even if the Sigma formulation is sometimes successful at producing active tubulin, different batches vary widely and are inconsistent at best.

After the failures to successfully lyophilize tubulin in 1970 and 1972, Shelanski et al. in 1973 demonstrated the frozen liquid approach to tubulin storage. In this method, tubulin solution is rapidly frozen in liquid nitrogen and is stored at temperatures below −70° C. Presently, this is the accepted method for storage of tubulin. This method is unsuitable for high through-put screening and other uses because retrieving the vials requires dexterity that cannot be automated easily. Another practical problem is the reproducibility of this method since the activity of preparations varies widely during the length of storage.

Prior to the invention disclosed herein, there remains a need for:

(1) lyophilized active tubulin that is highly active, stable and capable of providing reproducible results;

(2) lyophilized active tubulin that is competent of microtubule assembly;

(3) a lyophilization method for pure tubulin whereby tubulin can be lyophilized with high activity;

(4) appropriate vessels for lyophilization of tubulin so that the reconstituted form may be used for different applications; and (5) methods of high through-put screening methods for tubulin and tubulin ligands.

III. SUMMARY OF THE INVENTION

The present invention provides a formulation of tubulin that is stable, i.e., it will not denature and will maintain its activity, for greater than one year at room temperature, or alternatively for greater than five years at 4° C. This tubulin formulation is active once reconstituted and is capable of polymerizing to form microtubules. Currently available lyophilized forms of tubulin are impure ($\leq$40% purity), labile and unable to form microtubules. The level of stability provided by the lyophilized form of tubulin of the current invention will greatly increase the use of tubulin for applications such as research, drug discovery, diagnostics and therapy. Research applications include the possible use of the lyophilized active tubulin of the present invention to solve the three dimensional structure of tubulin (Nogales, E., Wolf, S. G., K. H. Downing, 1998, *Nature*, 391(6663), 199–203). The tubulin for the study conducted by Nogales et al., 1998, was supplied by Cytoskeleton, Inc. Drug discovery can be facilitated using the formulation of tubulin described in the invention as a substrate in high through-put screens for the development of new tubulin ligands. Diagnostic applications include the rapid assay of anti-tumor agents, e.g., paclitaxel, and anthlemintic agents, e.g., mebendazole. Potential therapeutic applications include the use of lyophilized tubulin in conjunction with or without anti-tubulin ligands in a complex encapsulated within a liposome. The liposome can serve as a vehicle of drug delivery.

The method of lyophilization and reconstitution described herein are breakthroughs in tubulin and tubulin ligand research and allow greater reproducibility and stability of this labile protein. Upon lyophilization, this method results in a highly active form of lyophilized tubulin that can be used with different isotypes, types, modified forms, purities, and recombinant forms of tubulin. Thus, this process is widely applicable to all forms of tubulin including microtubules formed from tubulin, MAP-rich tubulin (50% to 97% purified) (Shelanski et al. 1973), 97% to greater than 99% purified tubulin (e.g., Phospho-cellulose purified tubulin, Lee et al., 1978), tubulin in crude extracts (e.g., cancer cell line extracts), tubulin isolated from higher eukaryotes and their cell lines (Weatherbee et al. 1980; Morejohn and Fosket, 1982), tubulin isolated from fungi and yeasts and their cell lines (Davis et al. 1993), tubulin isolated from parasitic organisms or their cell lines (Dawson et al. 1983), and tubulins isolated from recombinant systems and recombinant organisms (Davis et al. 1994, Lubega et al. 1993).

The present invention covers different vessels for tubulin lyophilization since different applications of lyophilized tubulin require appropriate vessels for lyophilization and reconstitution. This includes single vials for all applications, wells in multi-well plates for high through-put screening and diagnostics, glass slides for microscopy research and diagnostics, solid supports such as dip sticks, filters, and the like, frozen drops of liquids that may be lyophilized for large quantity therapeutic applications, and any new vessels such as micro and nano-sized reaction chambers that may be available in the future.

The present invention includes the use of lyophilized active tubulin in a microtubule polymerization assay to measure the biological activity of tubulin. In this assay the optical density at $O.D._{340\ nm}$ is measured kinetically over time to determine polymerization and depolymerization. This kinetic assay can also be conducted at different temperatures to determine the stability of various forms of tubulin in comparison to the stable, active form of lyophilized tubulin of the present invention.

To facilitate the use of lyophilized active tubulin for the diagnostic application of assaying effective concentrations of anti-tumor agents like paclitaxel or anthlemintic agents like mebendazole, the present invention provides a high-throughput assay designed to measure anti-tubulin ligands. This assay can be used to measure ligand concentrations in body fluids such as serum, urine, and the like, fermentor broths, and to understand steps in the synthesis of ligands.

The present invention also covers potential therapeutic applications involving the use of lyophilized active tubulin, for example, the encapsulation within a microsomal liposome of a complex of tubulin and tubulin ligands to aid in drug delivery mechanisms.

IV. DESCRIPTION OF THE DRAWINGS

FIG. 1—Illustrates the effect of lyophilization constituents on the short term stability of lyophilized tubulin. Procedures for lyophilization of MAP-rich tubulin are described in V3. The dried powder was resuspended at 1 mg/ml protein in G-PEM and incubated at 24° C. for 1 hr. The optical density difference was determined between T=0 and T=60 minutes and that is plotted on the chart.

FIG. 2—Shows the reconstitution study for lyophilized tubulin. Procedures for lyophilization of MAP-rich tubulin are described in V3 and the optimal buffer was used for all samples. The dried powder was resuspended at 1 mg/ml protein in the noted buffers and incubated at 24° C. for 1 hr. The optical density difference was determined between T=0 and T=60 minutes and that is plotted on the chart.

FIG. 3—Is a comparative illustration of a frozen vs. air-dried study for lyophilized tubulin. Procedures for lyophilization of MAP-rich tubulin are described in V3 and the optimal buffer was used for all samples. The dried powder was resuspended at 1 mg/ml protein in the G-PEM buffer and incubated at 24° C. for 1 hr. The optical density ("OD") difference was determined between T=0 and T=60 minutes and the Maximum OD are plotted on the chart.

FIG. 4—Illustrates the stability of lyophilized active tubulin over time compared using O.D., measured at $340_{nm}$. Procedures for lyophilization of MAP-rich tubulin are described in V3 and the optimal buffer was used for all samples. The dried powder was resuspended at 1 mg/ml protein in the G-PEM buffer and incubated at 24° C. for 1 hr. The optical density difference was determined between T=0 and T=60 minutes and the Onset (time to pass a certain OD, which=0.1× the maximum OD of the fully active protein), Polymerization rate (mOD/min) and the Maximum OD are plotted on the charts.

FIG. 5—Compares the estimated tubulin purity of Sigma T4925 tubulin with lyophilized active tubulin at 70%, 97% and >99% purity using SDS-PAGE (coomassie-blue stain). Samples of T4975 (Sigma Chemical Co.), ML113, TL97 and TL238 (Cytoskeleton Inc.) were run on a 10% polyacrylamide gel and stained with coomassie blue. 100 ug of protein was loaded for each sample. Estimated purity with respect to turbulin is 30–40% for T4975, 50–70% for ML113, 95–99% for TL97 and >99% for TL238.

FIG. 6—Compares the polymerization of Sigma T4925 tubulin, freshly purified tubulin and lyophilized active tubulin. Procedures for lyophilization of MAP-rich tubulin are described in V3 and the optimal buffer was used for all samples. The dried powder was resuspended at 5 mg/ml protein at 4° C. in a G-PEM buffer and then incubated at 24° C. for 1 hr. The optical density 340 nm was determined between T=O and T=60 min.

FIG. 7—Illustrates a negative stain electron photomicrograph (28,000 magnification) of microtubules made from various sources of tubulin. Electron microscopy was performed by uranyl acetate negative staining of tubulin samples incubated at 37° C. for 1 h. Magnification is x28000. Procedures for lyophilization of MAP-rich tubulin are described in V3 and the optimal buffer was used for all samples. The dried powder was resuspended to 1 mg/ml protein in the G-PEM buffer. Tubulin from Sigma Chemical Co. was prepared in accordance with the company's information sheet provided with the product.

FIG. 7a—Freshly prepared MAP-rich tubulin

FIG. 7b—Illustrates a negative stain electron photomicrograph (28,000 magnification) of microtubules from lyophilized active tubulin. Lyophilized MAP-rich tubulin.

FIG. 7c—Shows an electron micrograph of Sigma's tubulin preparation after incubation at 37° C. for 1 hour (28,000 magnification). T4975 tubulin from Sigma Chemical Co.

FIG. 8—Shows sample results of a 96 well plate assay with lyophilized tubulin. Procedures for lyophilization of MAP-rich tubulin are described in V3 and the optimal buffer was used for all samples. The dried powder was resuspended to 1 mg/ml protein in the G-PEM buffer and incubated at 24° C. for 1 h. The optical density was determined between T=O and T=60 min.

FIG. 9—Shows sample results of a 96 well plate assay with lyophilized tubulin and duplicate reactions. Procedures for lyophilization of MAP-rich tubulin are described in V3 and the optimal buffer was used for all samples. The dried powder was resuspended to 1 mg/ml protein in the G-PEM buffer that contained different tubulin ligands. The reactions were incubated at 24° C. and the optical density was determined between T=O and T=60 min. Wells A1, A2—duplicate control reactions; wells B1, B2—Duplicate 3 uM nocodazole reactions, and wells C1, C2—Duplicate 3 uM paclitaxel reactions. Other duplicate wells contained buffer with a random concentration of nocodazole between 0–30 uM.

FIG. 10—Shows the Effect of TAXOL concentration on the polymerization rate of a prepared sample (No. ML113) of lyophilized active tubulin. Similar protocols were performed as in FIG. 9 legend except that paclitaxel was present at different concentrations and assays were performed in triplicate. Average nucleation (Onset) times, polymerization rates and maximum OD340 nm were compared to the control reactions (no drug) using CytoDYNAMIX Screen™ data analysis package (Cytoskeleton, Inc.).

FIG. 11—Shows the Effect of nocodazole concentration on the polymerization rate of a prepared sample (No. ML113) of lyophilized active tubulin. Similar protocols were performed as in FIG. 9 legend except that nocodazole was present at different concentrations and assays were performed in triplicate. Average nucleation (Onset) times, polymerization rates and maximum OD340 nm were compared to the control reactions (no drug) using CytoDYNAMIX Screen™ data analysis package (Cytoskeleton, Inc.).

FIG. 12—Illustrates how modified tubulins retain polymerization activity after lyophilization. Unlabeled, biotin and rhodamine conjugated tubulins (see Cytoskeleton catalogs 1994, 1995, 1996, 1997 and 1998) were lyophilized with the preferred procedure. Samples were reconstituted with the preferred buffer and placed on ice. Samples were centrifuged at 100,000×g for 30 min at 4° C. to pellet denatured protein. The supernatant was polymerized by incubating at 37° C. for 40 min and centrifuged again at 100,000×g for 30 min at 37° C. for 40 min and centrifuged again at 100,000×g for 30 min at 37° C. The protein was determined by Bradford assay for the denatured protein, polymer pellet and supernatant.

FIG. 13—Illustrates how other sources of tubulin are amenable to lyophilization. Bovine brain, Hela cell line (cancer cell line), Yeast and mutated yeast tubulins (see Cytoskeleton catalogs 1995, 1996, 1997 and 1999) were lyophilized with the preferred procedure, 200 ug each. Samples were reconstituted with 100 ul of the preferred buffer and placed on ice. Samples were centrifuged at 100,000×g for 30 min at 4° C. to pellet denatured protein. The supernatant was polymerized by incubating at 37° C. for 40 min and centrifuged again at 100,000×g for 30 min at 37° C. The protein was determined by Bradford assay for the denatured protein, polymer pellet and supernatant.

FIG. 14—Shows Microtubules before and after lyophilization. Greater than 97% purified tubulin was incubated at 5 mg/ml in G-PEM plus 5% sucrose and 1% FICOLL for 30 min at 37° C. At this time paclitaxel was added to 10 uM final concentration and the reaction continued for 10 min. A sample was taken and processed for electron microscopy (a) and the rest was lyophilized at 10 ug per well in a 96-well plate by the preferred procedure except the buffer is that of the reaction stated here. After reconstitution in nano-pure water to 5 mg/ml another sample was taken and processed for electron microscopy (b).

V. DETAILED DESCRIPTION OF THE INVENTION

The present invention provides a formulation of lyophilized tubulin that is stable for greater than one year at room temperature, or alternatively for greater than five years at 4° C. This tubulin formulation is active once reconstituted and is capable of polymerizing to form microtubules. The present invention includes a method for producing this formulation of lyophilized tubulin. The method includes the following steps: Isolation by standard methods, purification by cycles of microtubule polymerization and depolymerization, differential sedimentation centrifugation, suspension of the tubulin in a formulation containing a buffer, a salt, a nucleotide, a sugar and a carbohydrate polymer or a combination of some of these, lyophilization of the tubulin at a high concentration, storage of the tubulin and reconstitution of the tubulin in an active form. The reconstituted tubulin is then tested for biological activity using a microtubule polymerization assay. This assay has been optimized to measure differences between the control and test reactions as detailed in the copyrighted manual for high through put screens called "CytoDYNAMIX Screens™." Microtubule formation is further tested by electron microscopy. Comparative studies between the lyophilized tubulin product, Catalog No. T4975, sold by Sigma Chemical Company, and the lyophilized tubulin of the present invention show that microtubules are much less abundant with the T4975 product and the microtubules that do form are coated with denatured protein aggregates that suppress its biological activity and dynamic nature.

V.(1) Isolation of Tubulin

Tubulin can be isolated from most eukaryotic and some recombinant prokaryotic sources by standard methods. Various degrees of purity are produced by these methods. (Weisenberg and Timasheff, 1970; Weatherbee et al. 1980; Davis et al. 1993; Barnes, G., Louie, J. M., D. Botstein, 1992, *Biochemistry*, 32, 8823–8835; Lubega, G. W., Geary, T. G., Klein, R. D., R. K. Prichard, 1993, *Mol. Biochem. Parasitol.*, 62, 281–292.) Tubulin is isolated as MAP-rich bovine brain tubulin (Shelanski et al. 1973) by three cycles of polymerization and depolymerization, greater than 99% purified bovine brain tubulin (phospho-cellulose purified tubulin by the method of Lee et al. 1978), DEAE-Cellulose purified Hela S3 Cell line tubulin (Weatherbee et al. 1980), and DEAE-Cellulose purified yeast and recombinant yeast tubulin (Davis et al. 1993).

V.(2) Modified Forms of Tubulin

There are currently several types of chemically and enzymatically modified tubulins reported in the literature. Modified tubulins include biotinylated, fluorescent, tyrosinylated, non-tyrosinylated, acetylated, caged fluorescence and fluorescent analog derivatives. The lyophilization procedure described in Section V.(3) below has been tested on biotinylated and fluorescent derivatives. These derivatives are made stable by the lyophilization process (See FIG. 12), and, thus, have an increased shelf life as compared to non-lyophilized samples.

V.(3) Lyophilization Procedure

The process of producing lyophilized active tubulin of the present invention can be applied to all isotypes, types, modified forms, recombinant forms, and all purity levels of tubulin since it has been performed on MAP-rich bovine brain tubulin, 70% pure and greater than 99% purified bovine brain tubulin, DEAE-Cellulose purified Hela S3 Cell line tubulin, DEAE-Cellulose purified yeast and recombinant yeast tubulin (70%–95% purity). The activity of the lyophilized tubulin product is extremely high, i.e., greater than 95% activity.

Tubulin is purified by one of the methods described in Section V.(1), above, by successive cycles of polymerization and depolymerization. Active tubulin will polymerize to form microtubules which are separated from non-polymerized tubulin by differential sedimentation centrifugation which sediments the microtubules into a pellet at the bottom of the centrifuge tube. The supernatant is then removed and the tube containing the pellet is placed on ice. The pellet is then resuspended in a lyophilization buffer at concentrations between 1 µg/ml to 200 mg/ml and placed into a vessel for lyophilization.

Tubulin at 0.2 to 50 mg/ml is polymerized by incubating at a temperature from 4° C. to 45° C. for 1 to 500 minutes, and more preferably, at a temperature of 37° C. Preferably, the number of cycles of polymerization can be 1 to 6, and more preferably, about 2 to 3 for higher yields. The preferred temperature gradient for polymerization is usually less than 5 minutes from the low temperature to the high temperature. Polymerization at the increased temperature is preferably, from 1 to 500 minutes, more preferably, from 20 to 120 minutes, and most preferably, at 45 minutes. The concentration of tubulin during polymerization is preferably, between 0.2 to 50 mg/ml, more preferably, between 0.5 to 20 mg/ml, and most preferably, at 5 mg/ml.

Preferably, the temperature for centrifugation is between 15° C. to 45° C., and more preferably, the temperature is 37° C. Preferably, the sample is centrifuged at 5,000×g to 500,000×g, more preferably, 30,000×g to 200,000×g, and most preferably, at 100,000×g. The period of centrifugation is preferably, for 5 to 5000 minutes, more preferably, for 10 to 1000 minutes and, most preferably, for 30 minutes. The supernatant is removed by decanting and the tube containing the pellet is placed on ice.

Prior lyophilization methods for tubulin have been unsuccessful. The present invention produces highly active lyophilized tubulin and is applicable to a wide range of uses. This invention disclosed herein illustrates that tubulin that is lyophilized at higher concentrations is more active than tubulin lyophilized at lower concentrations. It was determined that there was a 40% loss in activity for tubulin at 3 mg/ml compared to 20 mg/ml. Thus, the concentration at which the pellet is resuspended prior to lyophilization is very critical. Preferably, pellet resuspension can be at a protein concentration of 1 µg/ml to 200 mg/ml, more preferably, between 0.5 to 50 mg/ml, and most preferably, at 20 mg/ml.

The tubulin lyophilization solution includes a buffer, a sugar, a carbohydrate polymer, a nucleotide, and a substitute protein. Buffers include, but are not limited to, PIPES, MES, Tris buffer and phosphate buffer. Preferably, the buffer is PIPES at a concentration of 15 mM, pH 6.9. Sugars include but are not limited to, sucrose, glucose, maltose and galactose. Preferably, the sugar is sucrose at 5% w/v. Carbohydrate polymers include, but are not limited to, dextran, polyethylene glycol and FICOLL. Preferably, the carbohydrate polymer is FICOLL™ (400 Kdal) at 1% w/v. Salts include, but are not limited to, $MgCl_2$, $MnCl_2$, $CaC_2$, and magnesium acetate. Preferably, the salt is $MgCl_2$, at 0.5 mM. Nucleotides include, but are not limited to, adenosine triphosphate (ATP), guanosine triphosphate (GTP), and guanosine diphosphate (GDP). Preferably, the nucleotide is GTP, at 0.5 mM. Substitute proteins include, but are not limited to, Bovine Serum Albumin (BSA) and Imunoglobulins like IgG. Preferably, the substitute protein is BSA, at 10 mg/ml. These substitute proteins can substitute for up to 50% of tubulin. Alternatively, the pellet may also be suspended in distilled water alone for a semi-stable, less than optimal formulation.

The pellet is preferably air-dried or frozen; more preferably it is air-dried. Lyophilization is conducted preferably at a temperature between −200° C. to 60° C., more preferably at −45° C. to 30° C., and most preferably at −40° C. for frozen samples and 4° C. for air-dried liquid samples. The water content (v/v) in the sample is preferably between 0% to ran 20%, more preferably between 0.2% to 5%, and most preferably between 1% to 3%. Lyophilization is preferably performed at a vacuum pressure between 76 torr to 1 milli-torr, more preferably between 10 torr to 20 milli-torr, and most preferably at 100 milli-torr.

V.(4) Vessels for Lyophilization

Different applications for lyophilized tubulin require different vessels for lyophilization of tubulin. The vessels include, but are not limited to, single vials for all applications, wells in 96-well, 384-well, 864-well and higher well plates, wells and walls of the wells in 96-well, 384-well, 864-well and higher well plates, glass slides, solid supports, dip sticks, filters, frozen liquid drops, and any micro or nano-sized reaction chambers that may be available in the future.

V.(5) Storage of Lyophilized Tubulin

After lyophilization the product can be stored at −189° C. to 37° C. with desicant for greater than one year (See FIG. 3) which can be extrapolated to greater than five years at 4° C. Prior storage methods involved freezing tubulin solution in liquid nitrogen and storing at −70° C. (Shelanski et al. 1973). Storage at −70° C. is unsuitable for high through-put screening and other uses because retrieving the vials requires dexterity that cannot be automated easily. Thus, the lyophilization and subsequently, the storage methods of the present invention offer significant advantages over the methods described in the prior art.

V.(6) Reconstitution of Tubulin

Present reconstitution methods involve reconstitution of tubulin that is either impure, or has variable or no activity. The present invention includes a novel reconstitution method that maintains high activity of the protein. Reconstitution of the pellet is conducted with a standard tubulin buffer that includes a buffer, a salt, a triphosphate nucleotide, a calcium chelator and a water exclusion agent that also promotes microtubule assembly. Buffers include, but are not limited to, PIPES, MES, Tris buffer and phosphate buffer. Preferably, the buffer is PIPES at a concentration of 80 mM. Salts include, but are not limited to, $MgCl_2$, $MnCl_2$, $CaCl_2$, and magnesium acetate. Preferably, the salt is $MgCl_2$, at 1.0 mM. Triphosphate nucleotides include, but are not limited to, GTP, ATP, GMP and GDP. Preferably, the triphosphate nucleotide is GTP, at 1.0 mM. The calcium chelator is preferably EGTA. Water exclusion agents include, but are not limited to, sucrose, glucose, poly-ethylene glycol and glycerol. Preferably, the water exclusion agent is glycerol, at a concentration of 0% to 10%.

V.(7) Testing the Biological Activity of Tubulin

Another aspect of this invention is an assay by which to test the biological activity of tubulin.

Microtubule Polymerization Assay

In this assay a solution of tubulin is warmed to 37° C. in a spectrophotometer in the presence of GTP. Over time, the tubulin polymerizes to form microtubules which refract light at 340 nm thus increasing the optical density. The optical density is proportional to the concentration of microtubule polymers, where 1.0 O.D.$_{340\ nm}$ over 1 cm pathlength=5.5 mg/ml microtubule polymer. Inactive tubulin will not show an increase in optical density over a 60 minute time period. This assay can be used to compare lyophilized formulations of tubulin to determine activity (e.g., FIG. 6).

A second test to determine the formation of bonafide microtubules involves placing the tubulin microtubule mixture on ice to see if the microtubules will depolymerize and reduce their measured optical density to the original value. The microtubule mixture is then reheated to 37° C. to polymerize again. The lyophilized active tubulin of the present invention performs this standard assay very well. Thus, these assays can be used to test the activity of different preparations of tubulin, to test the efficacy of anti-tubulin ligands, anti-tubulin antibodies, etc., and to test the stability of lyophilized active tubulin.

Testing the Stability of Lyophilized Active Microtubules

In another embodiment of this invention, microtubules can be stabilized by the addition of paclitaxel. Paclitaxel is added to a solution of microtubules which is then lyophilized under the optimal conditions described in the present invention (see FIG. 14). These lyophilized microtubules are then used for high through-put screening for microtubule motor ligands, e.g., kinesin, since microtubules are the substrate for molecular motor activity.

V.(8) High Through-put Screening

In yet another embodiment of this invention, the lyophilization procedure is conducted on tubulin in 96-well plates to show the applicability of this method to high through-put screening. Paclitaxel is added to the lyophilized active tubulin as a positive control since it promotes microtubule formation. Nocodazole is similarly used as a negative control since it depolymerizes microtubules. Substances that may potentially have an effect on microtubule polymerization can be assayed by this method in which the optical density was measured at 340 nm over 60 minutes at a temperature sufficient to support polymerization (i.e., 15–45° C., preferably 24° C. for MAP-rich or 37° C. for pure tubulin). These substances include, but are not limited to, prepared plant extracts, tubulin ligands, synthetic molecules, molecules prepared from a combinatorial library, small organic molecules, molecular motor proteins, microtubule associated proteins, proteins that interact with microtubules and/or tubulin like kinesins, dyneins, MAPs, MAP2s, onc 18, XKCM-1, CENP-E, and their homologues, GTPase activated or fluorescent analogs, or any other proteins that use lyophilized and reconstituted microtubules or tubulin as their substrates. The method of preparation described here creates a very accurate assay, the coefficients of variation for the nucleation, polymerization and steady state phases of microtubule polymerization are 13.6, 7.5, and 9.2, respectively.

V.(9) Diagnostic Applications with Lyophilized Active Tubulin

In a further embodiment of this invention, lyophilized active tubulin can be used for the diagnostic application of measuring anti-tubulin ligands that include, but are not limited to, TAXOL (paclitaxel) and mebendazole. The assay may be used to measure these ligands in body fluids, fermentor broths, and in steps of synthesis of ligands. The assay may be conducted in a vessel that includes, but is not limited to, a 96-well plate.

V.(10) Therapeutic Applications with Lyophilized Active Tubulin

Lyophilized active tubulin may also be used for therapeutic applications. Lyophilized active tubulin can be used in conjunction with or without tubulin ligands in a complex for therapeutic purposes. In one embodiment of this invention, Paclitaxel stabilized microtubules can be made by reconstitution of lyophilized active tubulin into TAXOL containing buffer and encapsulating them into liposomes. The liposomes will serve as the vehicle of delivery for the slow drug delivery of tubulin ligands.

This invention is illustrated in the examples which follow. The examples are set forth to give an understanding of the invention, but are not intended to, and should not be construed to limit in any way the invention as set forth in the claims which follow thereafter.

EXAMPLE 1

Determining the Optimal Conditions for Lyophilization of Tubulin

The temperature and vacuum pressure at which lyophilization was conducted was optimized by studying the effects on tubulin competence after lyophilization. Tubulin was suspended in the preferred lyophilization buffer at 20 mg/ml. Lyophilization was conducted at −40° C., −10° C., 4° C., 10° C., 24° C., 37° C. and 60° C. Upon completion of lyophiliza samples were stored at 37° C. for one week prior to assaying for polymerization activity. Frozen (rapid freezing in liquid nitrogen) and liquid forms of the preparation were tested over the same temperature profile.

The liquid form froze quickly after application of the vacuum at temperatures below 10° C. which stabilized the protein. At 24° C., 37° C., and 45° C., the liquid samples boiled vigorously and over-flowed the vessel (96-well plate).

The frozen forms at −40° C., −10° C., 4° C. and 10° C. stayed as a frozen solid (above 0° C. the evaporation of water from the samples reduces their energy, which makes them cooler than the surroundings). These samples reconstituted well and polymerized well. However, there was a slight reduction in activity compared to the air-dried sample. At 24° C., 37° C. and 45° C. the frozen samples turned liquid and boiled the contents, over flowing the vessel.

EXAMPLE 2

Effect of Protein, Buffer, Sugar, Carbohydrate Polymer, Salt and Triphosphate Nucleotide on Tubulin Lyophilization The optimal formulation was derived from the general tubulin buffer (80 mM Pipes pH6.9, 1 mNM MgCl$_2$, 1 mM EGTA and 1 mM GTP (Brinkley et al. 1978). The components were adjusted as described in FIGS. 1 and 2 with the addition of a freezing protectant (sugar) and a molecular motion inhibitor (long chain carbohydrate).

The constituents of the preferred buffer were tested for their affects on tubulin activity after lyophilization by using the polymerization assay. The tubulin pellet was resuspended in G-PEM buffer plus 5% sucrose and 1% FICOLL (400 Kdal) at 10 mg/ml, unless otherwise stated. This composition served as the control. The tubulin concentration was less than optimal (optimal=20 mg/ml), 10 mg/ml destabilized the protein enough to determine the importance of the buffer constituents. The samples were stored at 37° C. for one week prior to assaying for polymerization activity.

Reduction in tubulin or sucrose concentration reduced tubulin activity after lyophilization. Reduction in PIPES, Mg, or GTP increased tubulin activity after lyophilization.

EXAMPLE 3
Effect of Buffer, Calcium Chelator, Salt, Water Exclusion Agent and Triphosphate Nucleotide on Tubulin Reconstitution The constituents of the optimal reconstitution buffer were tested for their effects on tubulin activity after lyophilization by using the polymerization assay. 99% pure tubulin purified from bovine brain was suspended at 20 mg/ml in lyophilization buffer. The samples were stored at 37° C. for one week prior to assaying for polymerization activity. Reconstitution was done in the optimal buffer (as a control) and other buffer formulations, as indicated below, and in FIG. 2. It was determined that GTP, phosphate and Tris buffer all had a significant effect on activity.

The reconstitution buffers tested are as follows:

| | |
|---|---|
| G-PEM (Control): | 80 mM PIPES, pH 6.9, 1.0 mM $MgCl_2$, 1.0 mM GTP, 0.5 mM EGTA and 10% glycerol |
| PEM: | 80 mM PIPES, pH 6.9, 1.0 mM $MgCl_2$, 0.5 mM EGTA and 10% glycerol |
| G-PBS: | 50 mM Phosphate, pH 6.9, 50 mM NaCl, 1.0 mM $MgCl_2$, 1.0 mM GTP, 0.5 mM EGTA and 10% glycerol |
| PBS: | 50 mM Phosphate, pH 6.9, 50 mM NaCl, 1.0 mM $MgCl_2$, 0.5 mM EGTA and 10% glycerol |
| G-MEM: | 100 mM MES, pH 6.9, 1.0 mM $MgCl_2$, 1.0 mM GTP, 0.5 mM EGTA and 10% glycerol |
| MEM: | 100 mM MES, pH 6.9, 1.0 mM $MgCl_2$, 0.5 mM EGTA and 10% glycerol |
| G-TEM: | 80 mM Tris-HCl, pH 6.9, 1.0 mM $MgCl_2$, 1.0 mM GTP, 0.5 mM EGTA and 10% glycerol |
| TEM: | 80 mM Tris-HCl, pH 6.9, 1.0 mM $MgCl_2$, 0.5 mM EGTA and 10% glycerol |

EXAMPLE 4
Comparison of Frozen vs. Air-dried Study for Lyophilized Active Tubulin Polymerized tubulin was pelleted as described in Example 1 and resuspended in the preferred lyophilization formulation described in Example 2 at concentrations of 3 mg/ml and 20 mg/ml respectively. One milligram of each sample was drop frozen in liquid nitrogen in an eppendorf tube, and one milligram of each sample was placed in eppendorf tubes over ice. The samples were then lyophilized by the preferred method for frozen and air-dried liquid samples as described in Example 1. Samples were reconstituted as described in Example 3 and polymerized at 37° C. for 40 minutes. The maximum $O.D._{340\ nm}$ was compared between samples.

At a resuspension concentration of 3 mg/ml before lyophilization, the frozen sample polymerized approximately 44% less than the air-dried sample. At a resuspension concentration of 20 mg/ml before lyophilization, the frozen sample polymerized approximately 7% less than the air-dried sample. Results are shown in FIG. 10.

EXAMPLE 5
Testing the Biological Activity and Stability of Tubulin

The biological activity of tubulin is tested in two ways. In the first assay, a solution of tubulin is warmed to 37° C. in a spectrophotometer in the presence of GTP. Over time, the tubulin polymerizes to form microtubules which refract light at 340 nm thus increasing the optical density. The optical density is proportional to the concentration of microtubule polymers, where 1.0 $O.D._{340\ nm}$ over 1 cm path length=5.5 mg/ml microtubule polymer. Low potency tubulin (Sigma Chemical Company, St. Louis, Mo., Catalog. No. T4925) will show a small increase in optical density over a 60 minute time period (See FIG. 6). This assay can be used to compare the activity of different lyophilized formulations of tubulin.

In the second assay, the formation of bonafide microtubules is studied by placing the tubulin microtubule mixture on ice to see if the microtubules will depolymerize and reduce their measured optical density to the original value. The microtubule mixture is then reheated to 37° C. to polymerize again. The lyophilized active tubulin of the present invention performs this standard assay very well, whereas inactive tubulin (Sigma Chemical Company, St. Louis, Mo., Catalog. No. T4925) does not depolymerize and polymerize as described. Thus, these assays can be used to test the activity of different preparations of tubulin, to test the efficacy of anti-tubulin ligands, anti-tubulin antibodies, and the like.

The stability of lyophilized tubulin preparations was tested by the polymerization assay. Fourteen preparations of lyophilized tubulin were prepared as described in Example 1. One plate was placed at 4° C., one at 24° C., and the other at 37° C. After 0 to 370 days, duplicate samples were tested by the same polymerization assay for activity. The lyophilized tubulin of the present invention stored at 4° C., 24° C., and 37° C. was completely stable and predicted to retain polymerization activity for more than one year at room temperature (See FIG. 4).

EXAMPLE 6
Comparison of Microtubule Formation Between Lyophilized and Fresh Tubulin Active tubulin was lyophilized in single vials and reconstituted with G-PEM. After incubation at 37° C. for 30 minutes (See FIG. 6), it was determined that lyophilized active tubulin forms similar microtubules as seen under the electron microscope as those formed from freshly prepared tubulin (See FIG. 7). This indicates that lyophilized active tubulin is a high quality reagent suitable for drug discovery, research, therapeutics and diagnostic uses. T4975 tubulin, from Sigma Chemical Co., formed very few and irregular microtubules by the same procedure (See FIG. 7).

EXAMPLE 7
Comparison of Lyophilized Tubulin of the Present Invention With Lyophilized Tubulin, Catalog No. T4975, Sigma Chemical Company, St. Louis, Mo.

A comparative study was done with the lyophilized tubulin of the present invention with lyophilized tubulin sold by Sigma Chemical Company, St. Louis, Mo. (Catalog No. T4925, Lot No. 87H4024) which is approximately 30–40% pure tubulin (See FIG. 5), hereafter referred to as the Sigma tubulin. The Sigma tubulin has approximately 30% denatured protein as determined by solubilization of the preparation in double distilled water and centrifugation at 25,000×g at 4° C. for 30 minutes as per the manufacturer's protocol. The protein pellet (denatured protein fraction) contained 30% of the total protein. As a comparison, the tubulin of the present invention had less than 5% denatured protein.

The supernatant was then warmed to 37° C. to initiate polymerization. The optical density of the Sigma tubulin measured kinetically over time showed little if any polymerization. The optical density measured at 340 nm was very small, less than 0.01 $O.D._{340\ nm}$ (See FIG. 6). The same concentration of lyophilized tubulin of the present invention polymerized to greater than 85% ($O.D._{340\ nm}$ with 0.8 cm path length=0.62). This experiment was repeated thrice with similar results. Thus, the Sigma tubulin is a very low activity preparation of tubulin that was lyophilized by a non-optimal procedure. The components of the Sigma tubulin are 7.5 mg impure protein, 0.1 M MES buffer (pH 6.5), 1 mM EGTA, 0.5 mM $MgCl_2$, 0.1 mM EDTA, 2.5 M glycerol. Glycerol is a non-lyophilizing liquid component. It is believed that the Sigma tubulin is inactive due to the presence of glycerol which increases protein mobility and thus increases the rate of thermal denaturation, EGTA (a calcium chelator that also binds to $Mg_2+$ at high concentrations, as is present in the lyophilized state), and EDTA (a $Mg_2+$ chelator that binds two moles of $Mg_2+$ per mole of chelator). Since $Mg_2+$ is required for tubulin stability, the presence of these $Mg_2+$ binding substances affects stability of tubulin. Finally, the estimated concentration of tubulin T4925 prior to lyophilization is approximately 1 mg/ml, as determined by the dry powder ring mark on the side of the vessel. This concentration is too low to support the active structure of tubulin during lyophilization (see FIG. 1). The Sigma tubulin is not available in a 96-well or any other format and would not be suitable for research, drug screening, diagnostics and therapy with active tubulin.

The activity of the Sigma tubulin was compared with the tubulin of the present invention by observing microtubule formation under the electron microscope. Microtubules can be observed under the electron microscope as striated cylinders. The tubulin of the present invention forms microtubules with characteristic appearance (compare FIGS. 7*a* and 7*b*), whereas the Sigma tubulin had very few microtubules which were irregular due to aggregates of denatured protein (compare FIGS. 7*a* and 7*c*).

EXAMPLE 8
Drug Screening for Tubulin Ligands Using Lyophilized Active Tubulin The lyophilization procedure is conducted on tubulin in 96-well plates to show the applicability of this method to high through-put screening. MAP-rich tubulin (100 μg/well) was lyophilized under the optimal conditions described in Example 1, in a 96-well plate. Ninety-six wells in a 96-well plate of lyophilized tubulin can be simultaneously reconstituted and their polymerization measured (See FIG. 8). The coefficient of variation for this assay is 16%, 13% and 10% for single, duplicate and triplicate assays, respectively. In a similar manner, using an 8-channel hand held pipettor, various random nocodazole concentrations were tested for activity. In addition, controls were added to the assay. Paclitaxel was added to the lyophilized active tubulin as a positive control since it promotes microtubule formation. Nocodazole was similarly used as a negative control since it depolymerizes microtubules. The optical density was measured at 340 nm over 60 minutes at 24° C. as an indication of microtubule polymerization (See FIG. 9). It was observed that paclitaxel and nocodazole have enhancing and negative effects, respectively, as expected, where paclitaxel promotes microtubule formation and nocodazole depolymerizes microtubules. The various nocodazole solutions had various activities (See FIG. 9) which indicates that these extracts contain chemicals that affect microtubule polymerization. Chemicals detected by similar methods may be useful for therapeutic drug development.

EXAMPLE 9
Diagnostic Screening of Anti-tubulin Ligands

Paclitaxel and nocodazole, anti-tumor agents, were assayed in G-PER buffer with lyophilized active tubulin. In this experiment, MAP-rich tubulin was lyophilized at 100 μg/well in a 96-well plate with the optimal procedure as described in Example 1. Solutions of paclitaxel or nocodazole at various concentrations were pipetted into individual wells at 100 μl per well. The optical density was measured at $O.D._{340\ nm}$ over 20 minutes at 24° C. An increased rate of polymerization was observed as indicated by an increased optical density with increasing concentrations of paclitaxel (See FIG. 10). This increase was proportional to $\log_{10}$ [concentration of Paclitaxel]. A decrease in the rate of polymerization as indicated by a decreased optical density with increasing concentrations of nocodazole was observed (See FIG. 11). This decrease was proportional to $1/\log_{10}$ [concentration of nocodazole].

EXAMPLE 10
Preparation of Paclitaxel Stabilized Microtubules

Greater than 99% purified tubulin was polymerized in a solution made up of 3 mg/ml tubulin, 80 mM PIPES, pH 6.9, 1.0 mM $MgCl_2$, 1.0 mM GTP, 0.5 mM EGTA and 1.0 μM paclitaxel. The solution was incubated at 37° C. for 30 minutes. Upon incubation, 10 μM paclitaxel was added and mixed in. This was incubated for a further 10 minutes and either centrifuged to pellet the microtubules or used directly in the next step. Samples were checked for intact microtubules by observation under the electron microscope. Samples were then prepared for lyophilization by adding 0.5% FICOLL and 2.5% sucrose. Samples were lyophilized in a 96-well plate under the preferred conditions described in Example 2. The samples were then stored at 37° C. for one week. Samples were reconstituted in G-PER and small volumes were taken for electron microscopy observation. It was determined that microtubules were present before and after lyophilization indicating that microtubules can be successfully lyophilized with this procedure (See FIG. 14).

EXAMPLE 11
Stability of Modified Tubulins

The stability of modified tubulins after lyophilization was studied. The study was conducted on different sources of lyophilized tubulins. The tubulins studied were unlabeled tubulin (Cat. No. T238, Cytoskeleton, Inc., Denver, Colo.), Biotin-labeled tubulin (Cat. No. T333, Cytoskeleton, Inc., Denver, Colo.) and fluorescent labeled (covalently linked to rhodamine) tubulin (Cat. No. T331, Cytoskeleton, Inc., Denver, Colo.). The samples were pre-lyophilized by the manufacturer using a procedure in which the tubulin samples (20 mg/ml) in tubulin lyophilization solution (15 mM PIPES, pH 6.9, 5% w/v sucrose, 1% w/v FICOLL™ (400 Kdal), 0.5 mM $MgCl_2$, guanosine triphosphate, and BSA substitute protein) were lyophilized at a temperature of 4° C. and a vacuum pressure of 100 milli-torr.

Each of the samples were reconstituted with the tubulin reconstitution buffer (80 mM PIPES, pH 6.9, 1.0 mM $MgCl_2$, 1.0 mM Guanosine triphosphate (GTP), 1.0 mM EGTA, and to 5% glycerol), and placed on ice. The samples were centrifuged at 100,000×g for 30 minutes at 4° C. to pellet any denatured protein. The supernatant was then polymerized by incubating the sample at 37° C. for 40 minutes, and then centrifuged again at 100,000×g for 30 minutes at 37° C. Protein concentrations of the denatured protein, and the protein concentration in the supernatant and polymer pellet were determined by a standard Bradford Assay. The results are depicted in FIG. 12. In each of the samples, the level of denatured protein was less than 5%.

EXAMPLE 12
Stability of Tubulin Isolated from Varying Eukaryotic Sources

Tubulins can be isolated from the many eukaryotic sources, for example yeast, tetrahymena, mammalian brain and other mammalian tissues and cell lines. It was determined that these sources of tubulin were amenable to lyophilization since they retained their polymerization activity after lyophilization. The study was conducted on Hela Cell Tubulin (Cat. No. H001, Cytoskeleton, Inc., Denver, Colo.), bovine brain tubulin (Cat. No. T238 or T237, Cytoskeleton, Inc., Denver, Colo.), yeast tubulin (Cat. No. Y001, Cytoskeleton, Inc., Denver, Colo.), and mutated yeast tubulin (Cat. No. Y001-T27, Cytoskeleton, Inc., Denver, Colo.). The samples were pre-lyophilized by the manufacturer using a procedure in which the tubulin samples (20 mg/ml) in tubulin lyophilization solution (15 mM PIPES, pH 6.9, 5% w/v sucrose, 1% w/v FICOLL™ (400 Kdal), 0.5 mM $MgCl_2$, guanosine triphosphate, and BSA substitute protein), were lyophilized at a temperature of 4° C. and a vacuum pressure of 100 milli-torr.

A 200 µg sample of each of the above tubulin proteins was reconstituted in tubulin reconstitution buffer (80 mM PIPES, pH 6.9, 1.0 mM $MgCl_2$, 1.0 mM Guanosine triphosphate (GTP), 1.0 mM EGTA, and 5% glycerol), and placed on ice. The samples were centrifuged at 100,000×g for 30 minutes at 4° C. to pellet any denatured protein. The supernatant was then polymerized by incubating the sample at 37° C. for 40 minutes, and then centrifuged again at 100,000×g for 30 minutes at 37° C. Protein concentrations of the denatured protein, and the protein concentration in the supernatant and polymer pellet were determined by a standard Bradford Assay. The results are depicted in FIG. 13. In each of the samples, the level of denatured protein was less than 10%.

What is claimed is:

1. A method for the preparation of lyophilized active tubulin comprising the steps of;
   (a) running at least one cycle of polymerization and depolymerization of tubulin;
   (b) conducting differential sedimentation centrifugation to create a pellet of active tubulin;
   (c) re-suspending the pellet at tubulin concentration between 1 µg/ml and 200 mg/ml in a lyophilization solution comprising distilled water, 5% w/v sucrose, 1% w/v Ficoll, 15 mM Pipes at a pH of 6.9. 0.5 mM $MgCl_2$, and 0.5 mM GTP; and
   (d) lyophilizing the re-suspended pellet.

2. The method of claim 1, wherein the step of lyophilizing the re-suspended pellet is conducted in multi-well plates for high through-put screens.

3. The method of claim 1, wherein the step of lyophilizing the re-suspended pellet is conducted in lyophilization vessels selected from single vials, wells in 96-well, 384-well, 864-well and higher well plates, glass slides, solid supports, dip sticks, filters, frozen liquid drops, any micro or nano-sized reaction chambers, and combinations thereof.

4. The method of claim 1 wherein the step of lyophilizing the re-suspended pellet further comprises rapid-freezing the re-suspended pellet in liquid nitrogen.

5. The method of claim 1 wherein the step of lyophilizing the re-suspended pellet further comprises producing a lyophilization product having a purity of at least 50 percent.

6. The method of claim 1 wherein the step of lyophilizing the re-suspended pellet further comprises producing a lyophilization product having a purity of at least 70 percent.

7. The method of claim 1 wherein the step of lyophilizing the re-suspended pellet further comprises producing a lyophilization product having a purity of at least 90 percent.

8. The method of claim 1 wherein the step of lyophilizing the re-suspended pellet further comprises producing a lyophilization product having a purity of at least 99 percent.

9. The method of claim 1 wherein the step of running at least one cycle of polymerization and depolymerization comprises multiple cycles of polymerization and depolymerization.

10. A method for producing an active tubulin comprising the steps of:
    (a) running at least one cycle of polymerization and depolymerization of tubulin;
    (b) conducting differential sedimentation centrifugation to create a pellet of active tubulin;
    (c) re-suspending the pellet at tubulin concentration between 1 µg/ml and 200 mg/ml in a lyophilization solution comprising distilled water, 5% w/v sucrose, 1% w/v Ficoll, 15 mM Pipes at a pH of 6.9, 0.5 mM $MgCl_2$, and 0.5 mM GTP;
    (d) lyophilizing the re-suspended pellet; and
    (e) reconstituting the lyophilized tubulin in a reconstitution solution comprising a buffer, a salt, a triphosphate nucleotide, a calcium chelator, and a water excluding agent, thereby producing an active tubulin solution.

11. The method of claim 10, wherein the step of lyophilizing is conducted in multi-well plates for high through-put screens.

12. The method of claim 10, wherein the step of lyophilizing the re-suspended pellet is conducted in lyophilization vessels selected from single vials, wells in 96-well, 384-well, 864-well and higher well plates, glass slides, solid supports, dip sticks, filters, frozen liquid drops, any micro or nano-sized reaction chambers, and combinations thereof.

13. The method of claim 10 wherein the step of lyophilizing the re-suspended pellet further comprises rapid-freezing the re-suspended pellet in liquid nitrogen.

14. The method of claim 10 wherein the step of lyophilizing the re-suspended pellet further comprises producing a lyophilization product having a purity of at least 50 percent.

15. The method of claim 10 wherein the step of lyophilizing the re-suspended pellet further comprises producing a lyophilization product having a purity of at least 70 percent.

16. The method of claim 10 wherein the step of lyophilizing the re-suspended pellet further comprises producing a lyophilization product having a purity of at least 90 percent.

17. The method of claim 10 wherein the step of lyophilizing the re-suspended pellet further comprises producing a lyophilization product having a purity of at least 99 percent.

18. The method of claim 10 wherein the reconstitution solution comprises with 80 mM Pipes at pH 6.9 and 4° C., 1 mM $MgCl_2$, 1 mM EGTA, 1 mM GTP, and 5% volume to volume glycerol.

19. The method of claim 10 wherein the step of running at least one cycle of polymerization and de polymerization comprises multiple cycles of polymerization and depolymerization.

20. A method for lyophilizing active tubulin protein, comprising;
    (a) isolation of active tubulin protein from an organic source;
    (b) polymerization of the active tubulin protein;
    (c) sedimentation of the active tubulin protein;
    (d) re-suspension of the active tubulin protein at tubulin concentration between 1 µg/ml and 200 mg/ml in a lyophilization solution comprising distilled water, 5% w/v sucrose, 1% w/v Ficoll, 15 mM Pipes at a pH of 6.9, 0.5 mM $MgCl_2$, and 0.5 mM GTP; and
    (e) lyophilizing the active tubulin protein to produce a lyophilized product.

21. The method of claim 20 wherein the step of lyophilizing the active protein further comprises rapid-freezing t active tubulin protein in liquid nitrogen.

22. The method of claim 20, wherein the lyophilized tubulin protein has a purity of at least 50 percent.

23. The method of claim 20 wherein the lyophilized tubulin protein has a purity of at least 70 percent.

24. The method of claim 20 wherein the lyophilized tubulin protein has a purity of at least 90 percent.

25. The method of claim 20 wherein the lyophilized tubulin protein has a purity of at least 99 percent.

26. The method of claim 20, wherein the step of lyophilizing the active tubulin protein further comprises placing the lyophilization solution with the active tubulin protein in a vessel, wherein the vessel is a single vial, a single bottle, a 96-well plate, a 384-well plate, a micro-sized solid support, a nano-sized solid support, a sphere of frozen liquid, or the sphere of frozen liquid comprising tubulin pipetted into liquid nitrogen.

27. A method of lyophilizing and reconstituting active tubulin protein, comprising:

(a) isolation of active tubulin protein from an organic source;

(b) polymerization of the active tubulin protein;

(c) sedimentation of the active tubulin protein;

(d) re-suspension of the active tubulin protein at tubulin concentration between 1 $\mu$g/ml and 200 mg/ml in a lyophilization solution comprising distilled water, 5% w/v sucrose, 1% w/v Ficoll, 15 mM Pipes at a pH of 6.9, 0.5 mM $MgCl_2$, and 0.5 mM GTP;

(e) lyophilizing the re-suspended active tubulin protein; and (f) reconstituting the lyophilized active tubulin protein in a reconstitution solution to produce a reconstituted active tubulin protein.

28. The method of claim 27 wherein the step of lyophilizing the re-suspended active tubulin protein further comprises rapid-freezing the active tubulin protein in liquid nitrogen.

29. The method of claim 27 wherein the reconstituted active tubulin protein has a purity of at least 50 percent.

30. The method of claim 27 wherein the reconstituted active tubulin protein has a purity of at least 70 percent.

31. The method of claim 27 wherein the reconstituted active tubulin protein has a purity of at least 90 percent.

32. The method of claim 27 wherein the reconstituted active tubulin protein has a purity of at least 99 percent.

33. The method of claim 27 wherein the step of lyophilizing the re-suspended active tubulin protein further comprises placing the lyophilization solution with the active tubulin protein in a vessel, wherein the vessel is a single vial, a single bottle, a 96-well plate, a 384-well plate, a micro-sized solid support, a nano-sized solid support, a sphere of frozen liquid, or the sphere of frozen liquid comprising tubulin pipetted into liquid nitrogen.

34. The method of claim 27 wherein the reconstitution solution comprises with 80 mM Pipes at pH 6.9 and 4° C., 1 mM $MgCl_2$, 1 mM EGTA, 1 mM GTP, and 5% volume to volume glycerol.

\* \* \* \* \*